United States Patent
Rätzsch et al.

(10) Patent No.: US 6,818,768 B2
(45) Date of Patent: Nov. 16, 2004

(54) MIXTURES OF TRIAZINE DERIVATIVES FREE FROM POLYALKYLENE OXIDE

(75) Inventors: Manfred Rätzsch, Wilhering (AT); Martin Burger, Linz (AT); Manfred Arnold, Leissling (DE); Willy Frank, Bad Lauchstädt (DE)

(73) Assignee: Agrolinz Melamin GmbH, Linz (AT)

( * ) Notice: Subject to any disclaimer, the term of this patent is extended or adjusted under 35 U.S.C. 154(b) by 0 days.

(21) Appl. No.: 10/205,001

(22) Filed: Jul. 25, 2002

(65) Prior Publication Data

US 2003/0050474 A1 Mar. 13, 2003

(30) Foreign Application Priority Data

Jul. 26, 2001 (DE) ......................................... 101 36 322

(51) Int. Cl.[7] .............................................. C07D 251/70
(52) U.S. Cl. ...................... 544/196; 544/197; 544/204; 544/205; 544/206
(58) Field of Search ................................ 544/196, 197, 544/204, 205, 206, 194; 524/100

(56) References Cited

U.S. PATENT DOCUMENTS

| | | | |
|---|---|---|---|
| 3,143,548 A | | 8/1964 | Reid et al. |
| 3,399,151 A | * | 8/1968 | Kaiser et al. ................. 260/2.5 |
| 3,812,122 A | | 5/1974 | Lengsfeld ................. 260/249.6 |
| 4,356,304 A | | 10/1982 | Szita et al. .................. 544/196 |
| 4,886,882 A | | 12/1989 | Ebel et al. ................... 544/196 |
| 5,066,307 A | * | 11/1991 | Lees et al. ....................... 8/182 |
| 5,153,245 A | * | 10/1992 | Cipolli et al. ................ 524/100 |

FOREIGN PATENT DOCUMENTS

| | | | |
|---|---|---|---|
| DE | 2118868 | | 4/1971 |
| DE | 35 12446 A1 | * | 10/1986 |
| EP | 0 051734 A | | 5/1982 |
| EP | 0 200 906 A | | 11/1986 |
| EP | 0225433 | | 12/1989 |

OTHER PUBLICATIONS

Ullmanns Encyclopedia of Industrial Chemistry (1997), vol. A2, pp. 130–131.

Duroplaste, Kunststoff–Handbuch Bd. 10, pp. 994–997, Carl Hanser–Verlag Munchen 1999.

Rhodes et al.; "Synethesis of titanium (IV) complexes 2,6–dimethylaniline substituted amino alcohols and their utilization in ethylene polymerizations"—Journal of Organometallic Chemistry, Elsevier–Sequoia S.A. Lausanne, Switzerland, Bd. 625, Nr. 1, 15. Apr. 2001, pp. 95–100.

* cited by examiner

Primary Examiner—Venkataraman Balasubramanian
(74) Attorney, Agent, or Firm—Webb Ziesenheim Logsdon Orkin & Hanson, P.C.

(57) ABSTRACT

Mixtures of triazine derivatives free from polyalkylene oxide Mixtures of triazine derivatives free from polyalkylene oxide are produced from 20 to 70 percent by weight of triazine derivatives with hydroxyalkyl amino groups and 80 to 30 percent by weight of triazine derivatives with bis (hydroxyalkyl) imino groups by catalytic reaction of alkylpropylene oxides with triazine derivatives at a melamine derivative/alkylpropylene oxide molar ratio of 1:1.5 to 1:10 in the presence of metal alkyls, metal hydrides, metal alcoholates and/or metal alkylamides as catalysts.

The triazine derivative/hydroxy group mixtures free from polyalkylene oxide are particularly suited for producing plastic materials, flame retardants, additives, pharmaceuticals, textile auxiliaries, and paints or finishes.

10 Claims, No Drawings

MIXTURES OF TRIAZINE DERIVATIVES FREE FROM POLYALKYLENE OXIDE

BACKGROUND OF THE INVENTION

1. Field of the Invention

This invention relates to mixtures of triazine derivatives with hydroxy groups free from polyalkylene oxide and a method of producing them.

2. Description of the Related Art

Triazine derivatives with hydroxy groups of the methylol melamine or methylol guanamine types that can be produced by reacting melamine or guanamine with formaldehyde are known (Ullmanns Encyclopedia of Industrial Chemistry (1987), Vol. A2, pp. 130–131; Duroplaste, Kunststoff-Handbuch Bd. 10, 994–997, Carl Hanser-Verlag München 1988]. These methylol melamines or methylol guanamines share the disadvantage of limited stability which may result in partial breaking back into melamine or guanamine and formaldehyde.

Also known are hydroxyoxaalkyl melamines in which the melamine amino group(s) are replaced by groups of the formula H—(—O—CHR'—CHR'—)$_n$ wherein R'=$C_1$–$C_4$ alkyl groups and n=2 or 3, and where said hydroxyoxaalkyl melamines are produced by reacting aminoethoxy ethanol with cyanuric chloride, dichloroaminotriazine or diaminochlorotriazine (EP 0 225 433). In addition to the great effort it takes to produce hydroxyoxaalkyl melamines, the general disadvantage is that this method cannot be used to produce hydroxyalkyl melamines with n=1.

Other known processes are reacting melamine with ethylene oxide in the presence of alkali metal hydroxides (DE 21 18 868) or reacting N,N'-hydroxyethyl melamines or N,N'-hydroxyaryl melamines with ethylene oxide or propylene oxide in the presence of sulfuric acid (U.S. Pat. No. 4,356,304). The disadvantage of these melamines modified by alkylene oxide to become melamine alkylpropylene oxide block copolymers lies in their long polyalkylene oxide sequences and in the interfering portions of unbound polyalkylene oxide.

SUMMARY OF THE INVENTION

The problem of this invention is to provide triazine derivatives with hydroxy groups that contain a high portion of hydroxyalkyl groups and no portion of polyalkylene oxides.

The problem of this invention was solved by polyalkylene oxide free mixtures of triazine derivatives with hydroxy groups consisting of a) 20 to 70 percent by weight of triazine derivatives with hydroxyalkyl amino groups of the formula

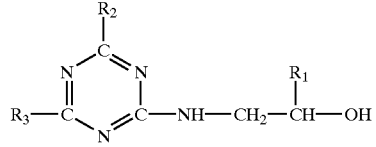

$R_1$=H or $C_1$–$C_4$ alkyl $R_2$=—H; —OH; $C_1$–$C_4$ alkyl, —$C_6H_5$; —$NH_2$; —NH—$CH_2$—$CHR_1$—OH; —NH—$CH_2$—$OR_1$, or —N(—$CH_2$—$OR_1$)$_2$, $R_3$=—H; —OH; $C_1$–$C_4$ alkyl, —$C_6H_5$; —$NH_2$; —NH—$CH_2$—$CHR_1$—OH; —NH—$CH_2$—$OR_1$, or —N(—$CH_2$—$OR_1$)$_2$, and b) 80 to 30 percent by weight of triazine derivatives with bis(hydroxyalkyl)imino groups of the formula

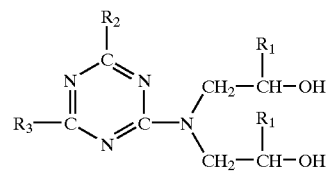

$R_1$=H or $C_1$–$C_4$ alkyl $R_2$=—H; —OH; $C_1$–$C_4$ alkyl, —$C_6H_5$; —$NH_2$; —NH—$CH_2$—$CHR_1$—OH, —N[$CH_2$—$CHR_1$—OH]$_2$, —NHCH$_2$—$OR_1$, or —N(—$CH_2$—$OR_1$)$_2$, $R_3$=—H; —OH; $C_1$–$C_4$ alkyl, —$C_6H_5$; —$NH_2$; —NH—$CH_2$—$CHR_1$—OH, —N[$CH_2$—$CHR_1$—OH]$_2$, —NHCH$_2$—$OR_1$, or —N(—$CH_2$—$OR_1$)$_2$.

DETAILED DESCRIPTION OF THE PREFERRED EMBODIMENTS

The following are examples of triazine derivatives replaced according to the invention by hydroxyalkyl amino groups and bis(hydroxyalkyl)imino groups: melamines, melamines replaced by amino-$C_1$–$C_{12}$-alkyl groups, diaminomethyl triazines such as 2,4-di(6-aminohexylamino)-1,3,5-triazine or diaminophenyl triazines, etherified methylol melamines, ammelines, ammelides, benzoguanamines, acetoguanamines, methoxymethyl benzoguanamines, caprinoguanamines and butyroguanamines whose amino groups are replaced both by hydroxyalkyl amino groups and bis(hydroxyalkyl) imino groups.

Preferred are mixtures of triazine derivatives and hydroxy groups free from polyalkylene oxide that consist of a) triazine replaced by hydroxyalkyl amino groups at a triazine/hydroxyalkyl amino group molar ratio from 1:1 to 1:2.5, and b) triazine replaced by bis(hydroxyalkyl) imino groups and hydroxyalkyl amino groups at a triazine/hydroxyalkyl group molar ratio from 1:2.5 to 1:5.5.

Examples of melamines replaced by hydroxypropyl amino groups or bis(hydroxyalkyl) imino groups are melamine derivatives of the following structures:

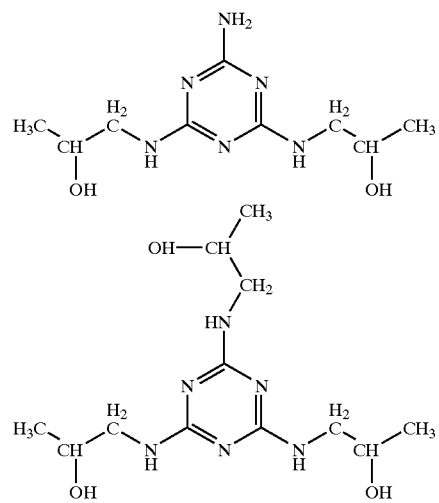

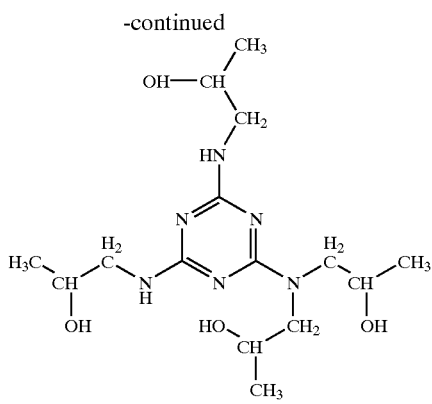

The mixtures of triazine derivatives and hydroxy groups free from polyalkyl oxide are produced according to the invention using a method in which mixtures consisting of a) 20 to 70 percent by weight of triazine derivatives with hydroxyalkyl amino groups of the formula

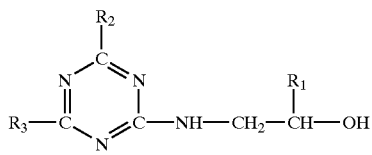

$R_1$=H or $C_1$–$C_4$ alkyl $R_2$=—H; —OH; $C_1$–$C_4$ alkyl, —$C_6H_5$; —$NH_2$; —NH—$CH_2$—$CHR_1$—OH; —NH—$CH_2$—$OR_1$, or —N(—$CH_2$—$OR_1$)$_2$, $R_3$=—H; —OH; $C_1$–$C_4$ alkyl, —$C_6H_5$; —$NH_2$; —NH—$CH_2$—$CHR_1$—OH; —NH—$CH_2$—$OR_1$, or —N(—$CH_2$—$OR_1$)$_2$, and b) 80 to 30 percent by weight of triazine derivatives with bis(hydroxyalkyl) imino groups of the formula

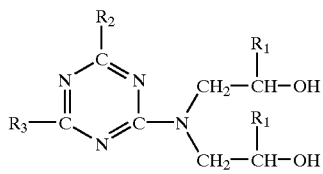

$R_1$=H or $C_1$–$C_4$ alkyl $R_2$=—H; —OH; $C_1$–$C_4$ alkyl, —$C_6H_5$; —$NH_2$; —NH—$CH_2$—$CHR_1$—OH, —N[$CH_2$—$CHR_1$—OH]$_2$, —$NHCH_2$—$OR_1$, or —N(—$CH_2$—$OR_1$)$_2$, $R_3$=—H; —OH; $C_1$–$C_4$ alkyl, —$C_6H_5$; —$NH_2$; —NH—$CH_2$—$CHR_1$—OH, —N[$CH_2$—$CHR_1$—OH]$_2$, —NH—$CH_2$—$OR_1$, or —N(—$CH_2$—$OR_1$)$_2$, are produced by catalytic reaction of alkylpropylene oxides of the formula

where $R_1$=H or $C_1$–$C_4$ alkyl with triazine derivatives of the formula

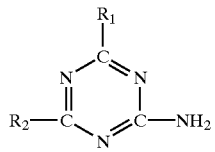

$R_1$=—H; —OH; $C_1$–$C_4$-Alkyl, —$C_6H_5$, —$NH_2$, —NH—$CH_2$—$OR_1$, or —N(—$CH_2$—$OR_1$)$_2$, $R_2$=—H; —OH; $C_1$–$C_4$-Alkyl, —$C_6H_5$, —$NH_2$; —NH—$CH_2$—$OR_1$, or —N(—$CH_2$—$OR_1$)$_2$, at a triazine derivative/alkylpropylene oxide molar ratio from 1:1.5 to 1:10 in the presence of 0.001 to 1 percent by weight—referred to the sum total of triazine derivative and alkylpropylene oxide—metal alkyls, metal hydrides, metal alcoholates and/or metal alkylamides as catalysts. The reaction takes place in polar anhydrous solvents of types such as dimethyl sulfoxide, tetramethylene sulfone, N-methyl pyrrolidine, dimethyl formamide and/or dimethyl acetamide at reaction temperatures from 35 to 150° C., pressures from 1 to 25 bar, and reaction times from 1 to 30 hours.

Suitable reactors for reacting the triazine derivatives with alkylpropylene oxides are stirred tanks with inert gas supply, vertical condenser, and bottom discharge valve.

It is advantageous after the reaction to process the reaction mixture by distilling off most of the solvent used in a vacuum, spray drying the solution of triazine derivative modified by alkylpropylene oxide, and optionally redrying it in a vacuum. Suitable triazine derivatives used for producing triazine derivatives with hydroxy groups and free from polyalkylene oxide include melamines, melamines replaced by amino $C_1$–$C_{12}$ alkyl groups, diaminomethyl triazines such as 2,4-di(6-aminohexylamino)-1,3,5-triazine, or diaminophenyl triazines, etherified methylol melamines, ammelines, ammelides, melem, melon, melam, benzoguanamine, acetoguanamine, methoxymethyl benzoguanamine, caprinoguanamine, and butyroguanamine.

The preferred triazine derivative used to produce triazine derivative/hydroxy group mixtures free of polyalkylene oxide according to the invention is melamine. Other triazine derivatives used to produce triazine derivative/hydroxy group mixtures free of polyalkylene oxide according to the invention are methylol melamines etherified using $C_1$–$C_8$ alcohols in which 1 to 5 hydrogen atoms of the melamine are replaced by $C_1$–$C_8$ alkyloxamethyl groups.

Preferred alkylpropylene oxides used in the method according to the invention to produce triazine derivative/ hydroxy group mixtures free of polyalkylene oxide are ethylene oxide and/or propylene oxide.

Suitable metal alkyls that can be used as catalysts in the method according to the invention to produce triazine derivative/hydroxy group mixtures free from polyalkylene oxide are lithium butyl, magnesium diethyl, zinc dimethyl, aluminum triisobutyl, boron triethyl, and titanium tetrabutyl.

Preferred metal alkyls are $C_1$–$C_4$ metal alkyls from alkali metals, particularly lithium alkyls.

Suitable metal hydrides that can be used as catalysts in the method according to the invention to produce triazine derivative/hydroxy group mixtures free from polyalkylene oxide are lithium hydride and sodium hydride.

Preferred metal alcoholates that are used as catalysts in the method according to the invention to produce triazine derivative/hydroxy group mixtures free from polyalkylene oxide are alcoholates of alkali metals, in particular, lithium methoxide, lithium-tert-butylate, sodium methoxide, sodium-tert-butylate and/or potassium-tert-butylate.

Other suitable metal alcoholates are alcoholates from thioalcohols such as lithium thiomethylate or potassium-tert-thiobutylate.

Suitable metal alkylamides that can be used as catalysts in the method according to the invention to produce triazine derivative/hydroxy group mixtures free from polyalkylene oxide are lithium dimethylamide, potassium diethylamide, and sodium diisopropylamide. Other suitable compounds are homologous phosphorus, arsenic, and antimony compounds such as lithium dimethyl phosphide or sodium diethyl arsenide.

When producing the triazine derivatives of the invention, a mixture is formed that is free of polyalkylene oxide byproducts. The composition of the mixture, i. e. the portions of triazine derivatives a) in which the hydroxyalkyl groups are exclusively bonded to the triazine rings as hydroxyalkyl amino groups, and the portions of triazine derivatives b) in which the hydroxyalkyl groups as well are bonded to the triazine rings as bis(hydroxyalkyl) imino groups as well as as hydroxyalkyl amino groups, is determined by the alkylpropylene oxide/triazine derivative ratio used for its production.

If the alkylpropylene oxide portion in the reaction mixture is low, the triazine derivative mixture with a high proportion of triazine derivatives a) in which the hydroxyalkyl groups are exclusively bonded to the triazine rings as hydroxyalkyl amino groups is formed.

If the alkylpropylene oxide portion in the reaction mixture is high, the triazine derivative mixture with a low proportion of triazine derivatives in which the hydroxyalkyl groups are exclusively bonded to the triazine rings as hydroxyalkyl amino groups and with a high portion of triazine derivatives b) in which the hydroxyalkyl groups as well are bonded to the triazine rings as bis(hydroxyalkyl) imino groups as well as as hydroxyalkyl amino groups is formed.

The overall portion of hydroxyalkyl groups bonded to the triazine ring in the triazine derivatives and the portion of hydroxyalkyl amino groups or bis(hydroxyalkyl) imino groups can be determined in an IR analysis. The individual species of triazine derivatives replaced by hydroxyalkyl groups and their portions in a mixture of triazine derivatives with hydroxyalkyl amino groups and bis(hydroxyalkyl) imino groups can be determined in a HPLC/MS analysis.

The triazine derivative/hydroxy group mixtures free from polyalkylene oxide are particularly suited for producing plastic materials, flame retardants, additives, pharmaceuticals, textile auxiliaries, and paints or finishes.

Production processes of plastics in which the triazine derivatives can be used as polyols include the production of polyurethanes by reaction with multifunctional isocyanates, the production of polyesters by reaction with multifunctional carboxylic acids, and the production of polyhydroxy ethers by reaction with polyfunctional glycidyl compounds.

The invention is explained in greater detail by the examples below.

EXAMPLE 1

After purging with inert gas, 12 l of dimethyl sulfoxide dried using a molecular sieve are filled into a 20 l pressurized autoclave equipped with a stirrer, vertical condenser, and bottom discharge valve. 1.26 kg of melamine is added and partially dissolved under intense stirring. 300 ml of the catalyst solution containing n-butyl lithium in cyclohexane (1.6 mol/l) are added by dropping to this suspension at room temperature. A reaction time of 20 minutes is sufficient for the formation of the lithium-melamine adduct. Subsequently, 1.74 kg of propylene oxide is put into the pressurized autoclave, and the pressurized autoclave is heated under stirring to a temperature of 85° C. while the internal pressure in the autoclave settles at 1.2 bar. The melamine is completely dissolved after 20 minutes, and after 10 hours at 85° C. a homogeneous, weakly cream-colored solution forms that is reduced to 6 l by distilling off most of the cyclohexane and dimethyl sulfoxide in a 12 mm Hg vacuum, and spray dried.

The yield of triazine derivative mixture is 92% of the quantity of propylene oxide used. An IR analysis reveals that 35 mole percent of the hydroxypropyl groups bonded to the triazine ring are hydroxypropyl amino groups, 65 mole percent are bis(hydroxypropyl) imino groups.

EXAMPLE 2

After purging with inert gas, 13 l of dimethyl sulfoxide dried using a molecular sieve are filled into a 20 l pressurized autoclave equipped with a stirrer, vertical condenser, and bottom discharge valve. A mixture of 756 g of melamine, 250 g of acetoguanamine and 29 g of dimethylol melamine dibutyl ether is added under intense stirring and partially dissolved. 330 ml of the catalyst solution containing isopropyl lithium in cyclohexane (1.5 mol/l) are added by dropping to this suspension at room temperature. A reaction time of 20 minutes is sufficient for the formation of the lithium adduct. Subsequently, 1.16 kg of propylene oxide is put into the pressurized autoclave, and the pressurized autoclave is heated under stirring to a temperature of 85° C. while the internal pressure in the autoclave settles at 1.2 bar. The mixture of melamine, acetoguanamine, and dimethylol melamine dibutyl ether is completely dissolved after 15 minutes, and after 12 hours at 85° C. a homogeneous, weakly cream-colored solution forms that is reduced to 5 l by distilling off most of the dimethyl sulfoxide and cyclohexane in a 12 mm Hg vacuum, and spray dried.

The yield of triazine derivative mixture is 96% of the quantity of propylene oxide used. An IR analysis reveals that 41 mole percent of the hydroxypropyl groups bonded to the triazine ring are hydroxypropyl amino groups, 59 mole percent are bis(hydroxypropyl) imino groups.

EXAMPLE 3

After purging with inert gas, 12 l of dimethyl formamide dried using a molecular sieve are filled into a 20 l pressurized autoclave equipped with a stirrer, vertical condenser, and bottom discharge valve. A mixture of 1.0 kg of melamine and 490 g of methoxymethyl benzoguanamine is added under intense stirring and partially dissolved. 500 ml of the catalyst solution containing boron triethyl in n-heptane (1.9 mol/l) are added by dropping to this suspension at room temperature. A reaction time of 40 minutes is sufficient for the formation of the boron adduct. Subsequently, 1.76 kg of ethylene oxide is put into the pressurized autoclave, and the pressurized autoclave is heated under stirring to a temperature of 80° C. while the internal pressure in the autoclave settles at 8 bar. The mixture of melamine and methoxymethyl benzoguanamine is completely dissolved after 30 minutes, and after 15 hours at 80° C. a homogeneous, weakly cream-colored solution forms that is reduced to 6 l by distilling off most of the heptane and the dimethyl formamide in a 8 mm Hg vacuum, and spray dried.

The yield of triazine derivative mixture is 88% of the quantity of ethylene oxide used. An IR analysis reveals that 28 mole percent of the hydroxyethyl groups bonded to the triazine ring are hydroxyethyl amino groups, 59 mole percent are bis(hydroxyethyl) imino groups.

EXAMPLE 4

After purging with inert gas, 12 l of dimethyl sulfoxide dried using a molecular sieve are filled into a 20 l pressurized autoclave equipped with a stirrer, vertical condenser, and bottom discharge valve. 1.26 kg of melamine is added and partially dissolved under intense stirring. 300 ml of the catalyst solution containing n-butyl lithium in cyclohexane (1.6 mol/l) are added by dropping to this suspension at room temperature. A reaction time of 20 minutes is sufficient for the formation of the lithium-melamine adduct. Subsequently, 3.48 kg of propylene oxide is put into the pressurized autoclave, and the pressurized autoclave is heated under stirring to a temperature of 85° C. while the internal pressure in the autoclave settles at 1.2 bar.

The melamine is completely dissolved after 20 minutes, and after 10 hours at 85° C. a homogeneous, weakly cream-colored solution forms that is reduced to 6.5 l by distilling off most of the cyclohexane and dimethyl sulfoxide in a 12 mm Hg vacuum, and spray dried.

The yield of triazine derivative mixture is 88% of the quantity of propylene oxide used. An IR analysis reveals that 23 mole percent of the hydroxypropyl groups bonded to the triazine ring are hydroxypropyl amino groups, 77 mole percent are bis(hydroxypropyl) imino groups.

EXAMPLE 5

After purging with inert gas, 12 l of dimethyl sulfoxide dried using a molecular sieve are filled into a 20 l pressurized autoclave equipped with a stirrer, vertical condenser, and bottom discharge valve. 1.26 kg of melamine is added and partially dissolved under intense stirring. 350 ml of a catalyst solution containing 40 g of lithium-tert-butylate in cyclohexane are added by dropping to this suspension at room temperature. After 30 minutes, 1.8 kg of propylene oxide is put into the pressurized autoclave, and the pressurized autoclave is heated under stirring to a temperature of 90° C. The melamine is completely dissolved after 20 minutes, and after 10 hours at 90° C. a homogeneous, weakly cream-colored solution forms that is reduced to 6.5 l by distilling off most of the cyclohexane and dimethyl sulfoxide in a 12 mm Hg vacuum, and spray dried.

The yield of triazine derivative mixture is 2.9 kg. An IR analysis reveals that 38 mole percent of the hydroxypropyl groups bonded to the triazine ring are hydroxypropyl amino groups, 62 mole percent are bis(hydroxypropyl) imino groups.

EXAMPLE 6

After purging with inert gas, 12 l of dimethyl sulfoxide dried using a molecular sieve are filled into a 20 l pressurized autoclave equipped with a stirrer, vertical condenser, and bottom discharge valve. 1.26 kg of melamine is added and partially dissolved under intense stirring. 300 ml of the catalyst solution containing 54 g of sodium methylate in cyclohexane are added by dropping to this suspension at room temperature. After 30 minutes, 1.45 kg of propylene oxide is put into the pressurized autoclave, and the pressurized autoclave is heated under stirring to a temperature of 100° C. The melamine is completely dissolved after 15 minutes, and after 3 hours at 100° C. a homogeneous, weakly cream-colored solution forms that is reduced to 6 l by distilling off most of the cyclohexane and dimethyl sulfoxide in a 12 mm Hg vacuum, and spray dried.

The yield of triazine derivative mixture is 2.61 kg. An IR analysis reveals that 40 mole percent of the hydroxypropyl groups bonded to the triazine ring are hydroxypropyl amino groups, 60 mole percent are bis(hydroxypropyl) imino groups.

EXAMPLE 7

After purging with inert gas, 12 l of dimethyl sulfoxide dried using a molecular sieve are filled into a 20 l pressurized autoclave equipped with a stirrer, vertical condenser, and bottom discharge valve. 1.26 kg of melamine is added and partially dissolved under intense stirring. 320 ml of a catalyst solution containing 56 g of potassium-tert-butylate in cyclohexane are added by dropping to this suspension at room temperature. After 30 minutes, 1.16 kg of propylene oxide is put into the pressurized autoclave, and the pressurized autoclave is heated under stirring to a temperature of 85° C. The melamine is completely dissolved after 20 minutes, and after 4 hours at 85° C. a homogeneous, weakly cream-colored solution forms that is reduced to 6 l by distilling off most of the cyclohexane and dimethyl sulfoxide in a 12 mm Hg vacuum, and spray dried.

The yield of triazine derivative mixture is 2.33 kg. An IR analysis reveals that 43 mole percent of the hydroxypropyl groups bonded to the triazine ring are hydroxypropyl amino groups, 57 mole percent are bis(hydroxypropyl) imino groups.

We claim:

1. Mixtures of Polyalkylene oxide-free triazine derivatives, each triazine derivative having hydroxy groups, wherein the mixtures consist essentially of
   a) 20 to 70 percent by weight of triazine derivatives with hydroxyalkyl amino groups of the formula

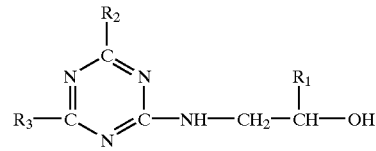

wherein
   $R_1$=H or $C_1$–$C_4$ alkyl,
   $R_2$=—H; —OH; $C_1$–$C_4$ alkyl, —$C_6H_5$; —$NH_2$; —NH—$CH_2$—$CHR_1$—OH; —NH—$CH_2$—$OR_1$, or —N(—$CH_2$—$OR_1$)$_2$,
   $R_3$=—H; —OH; $C_1$–$C_4$ alkyl, —$C_6H_5$; —$NH_2$; —NH—$CH_2$—$CHR_1$—OH; —NH—$CH_2$—$OR_1$, or —N(—$CH_2$—$OR_1$)$_2$, and
   b) 80 to 30 percent by weight of triazine derivatives with bis(hydroxyalkyl)imino groups of the formula

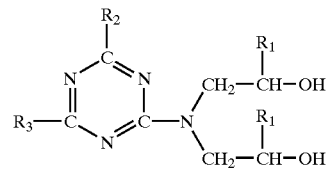

wherein
   $R_1$=H or $C_1$–$C_4$ alkyl,
   $R_2$=—H; —OH; $C_1$–$C_4$ alkyl, —$C_6H_5$; —$NH_2$; —NH—$CH_2$—$CHR_1$—OH, —NH[$CH_2$—$CHR_1$—OH]$_2$, —NH—$CH_2$—$OR_1$, or —N(—$CH_2$—$OR_1$)$_2$,
   $R_3$=—H; —OH; $C_1$–$C_4$ alkyl, —$C_6H_5$; —$NH_2$; —NH—$CH_2$—$CHR_1$—OH, —N[$CH_2$—$CHR_1$—OH]$_2$, —NH—$CH_2$—$OR_1$, or —N(—$CH_2$—$OR_1$)$_2$.

2. The mixtures of polyalkylene oxide-free triazine derivatives having hydroxy groups according to claim 1, wherein the mixtures consist essentially of
 a) triazine replaced by hydroxyalkyl amino groups at a triazine/hydroxyalkyl amino group molar ratio from 1:1 to 1:2.5, and
 b) triazine replaced by bis(hydroxyalkyl) imino groups and hydroxyalkyl amino groups at a triazine/hydroxyalkyl group molar ratio from 1:2.5 to 1:5.5.

3. A method of producing a polyalkylene oxide-free mixture of triazine derivatives having hydroxy groups, the method consisting essentially of
 a) catalytically reacting alkylene oxides of the formula

where $R_1$=H or $C_1$–$C_4$ alkyl with triazine derivatives of the formula

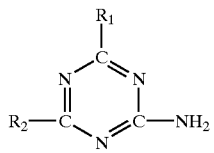

wherein
 $R_1$=—H; —OH; $C_1$–$C_4$-Alkyl, —$C_6H_5$, —$NH_2$; —NH—$CH_2$—$OR_1$, or —N(—$CH_2$—$OR_1$)$_2$,
 $R_2$=—H; —OH; $C_1$–$C_4$-Alkyl, —$C_6H_5$, —$NH_2$; —NH—$CH_2$—$OR_1$, or —N(—$CH_2$—$OR_1$)$_2$, at a triazine derivative/alkylpropylene oxide molar ratio from 1:1.5 to 1:10 in the presence of 0.00 1 to 1 percent by weight—referred to the sum total of triazine derivative and alkylene oxide—of one or more catalysts selected from the group consisting of metal alkyls, metal hydrides, metal alcoholates and metal alkylamides, said reaction taking place in one or more polar anhydrous solvents selected from the group consisting of dimethyl sulfoxide, tetramethylene sulfone, N-methyl pyrrolidine, dimethyl formamide and dimethyl acetamide,
 $R_3$=—H; —OH; $C_1$–$C_4$ alkyl, —$C_6H_5$; —$NH_2$; —NH—$CH_2$—$CHR_1$—OH; —NH—$CH_2$—$OR_1$, or —N(—$CH_2$—$OR_1$)$_2$, and
 b) 80 to 30 percent by weight of triazine derivatives with bis(hydroxyalkyl)imino groups of the formula

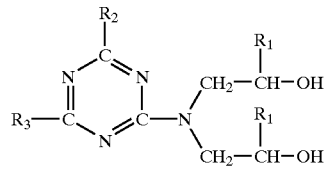

wherein
 $R_1$=H or $C_1$–$C_4$ alkyl,
 $R_2$=—H; —OH; $C_1$–$C_4$ alkyl, —$C_6H_5$; —$NH_2$; —NH—$CH_2$—$CHR_1$—OH, —N[$CH_2$—$CHR_1$—OH]$_2$, —NH—$CH_2$—$OR_1$, or —N(—$CH_2$—$OR_1$)$_2$,
 $R_3$=—H; —OH; $C_1$–$C_4$ alkyl, —$C_6H_5$; —$NH_2$; —NH—$CH_2$—$CHR_1$—OH, —N[$CH_2$—$CHR_1$—OH]$_2$, —NH—$CH_2$—$OR_1$, or —N(—$CH_2$—$OR_1$)$_2$.

4. The method of producing polyalkylene oxide-free mixtures of triazine derivatives having hydroxy groups according to claim 3, wherein the triazine derivative is melamine.

5. The method of producing polyalkylene oxide-free mixtures of triazine derivatives having hydroxy groups according to claim 3, wherein the triazine derivatives are methylol melamines etherified with $C_1$–$C_8$ alcohols such that 1 to 5 hydrogen atoms of the melamines are replaced by $C_1$–$C_8$ alkyloxamethyl groups.

6. The method of producing polyalkylene oxide-free mixtures of triazine derivatives having hydroxy groups according to claim 3, wherein the alkylene oxides are ethylene oxide and/or propylene oxide.

7. The method of producing polyalkylene oxide-free mixtures of triazine derivatives having hydroxy groups according to claim 3, wherein the metal alkyls are $C_1$–$C_4$ metal alkyls of alkali metals.

8. The method of claim 7, wherein the alkali metal is lithium.

9. The method of producing polyalkylene oxide-free mixtures of triazine derivatives having hydroxy groups according to claim 3, wherein the metal of the metal alcoholates is an alkali metal.

10. The method of claim 9, wherein the alkali metal is one or more selected from the group consisting of lithium methoxide, lithium-tert-butylate, sodium methoxide, sodium-tert-butylate and/or potassium-tert-butylate, are used as metal alcoholates.

* * * * *

UNITED STATES PATENT AND TRADEMARK OFFICE
CERTIFICATE OF CORRECTION

PATENT NO. : 6,818,768 B2
DATED : November 16, 2004
INVENTOR(S) : Rätzsch et al.

It is certified that error appears in the above-identified patent and that said Letters Patent is hereby corrected as shown below:

Column 8,
Line 63, "-NH[CH$_2$" should read -- N[CH$_2$ --

Signed and Sealed this

Seventeenth Day of May, 2005

JON W. DUDAS
*Director of the United States Patent and Trademark Office*